US006824075B2

(12) United States Patent
Zimmermann

(10) Patent No.: US 6,824,075 B2
(45) Date of Patent: Nov. 30, 2004

(54) SPRAY GUN

(75) Inventor: Guido Zimmermann, Friedrichshafen (DE)

(73) Assignee: J. Wagner GmbH, Markdorf (DE)

( * ) Notice: Subject to any disclaimer, the term of this patent is extended or adjusted under 35 U.S.C. 154(b) by 11 days.

(21) Appl. No.: 10/460,905

(22) Filed: Jun. 13, 2003

(65) Prior Publication Data

US 2004/0026534 A1 Feb. 12, 2004

(30) Foreign Application Priority Data

Jun. 15, 2002 (DE) ........................................ 102 26 792

(51) Int. Cl.[7] .......................... A62C 13/16; B05B 7/26; A61M 11/02

(52) U.S. Cl. ....................... 239/302; 239/314; 239/366; 239/368; 239/371; 239/291; 239/526

(58) Field of Search ................................ 239/302, 314, 239/315, 366, 368, 371, 291, 292, 296, 525, 526, 527; 222/391, 389, 335; 137/893; 251/320, 321, 322

(56) References Cited

U.S. PATENT DOCUMENTS 3,032,277 A * 5/1962 Petty .......................... 239/408
3,746,253 A * 7/1973 Walberg ..................... 239/705
5,671,888 A * 9/1997 Smith ......................... 239/415
5,685,482 A * 11/1997 Sickles .......................... 239/3
5,727,736 A * 3/1998 Tryon ......................... 239/345
RE35,769 E * 4/1998 Grime et al. ................. 239/72
5,803,372 A * 9/1998 Weinstein et al. .......... 239/703
6,425,533 B1 * 7/2002 Shilton et al. .............. 239/290

FOREIGN PATENT DOCUMENTS

| | | |
|---|---|---|
| DE | 35 18 492 C2 | 11/1986 |
| DE | 198 07 973 C1 | 7/1999 |
| DE | 198 14 532 A1 | 10/1999 |
| GB | 139833 | 3/1920 |

* cited by examiner

*Primary Examiner*—Michael Mar
(74) *Attorney, Agent, or Firm*—Pandiscio & Pandiscio

(57) ABSTRACT

A spray gun for atomizing fluid with compressed air comprises a housing having a handle, an atomizer nozzle, a guide sleeve having a U-shaped cross section which engages in the atomizer nozzle and is supported in the housing, and a valve needle which can be operated by means of a trigger which is in a pivoting mounting. The valve needle is connected with the trigger in the area of the guide sleeve by means of a hinge pin. A seal disposed in the guide sleeve, the seal being located between a feed line and the hinge pin, with the valve needle being held in a movable arrangement in the seal.

9 Claims, 3 Drawing Sheets

SPRAY GUN

Figure 1:
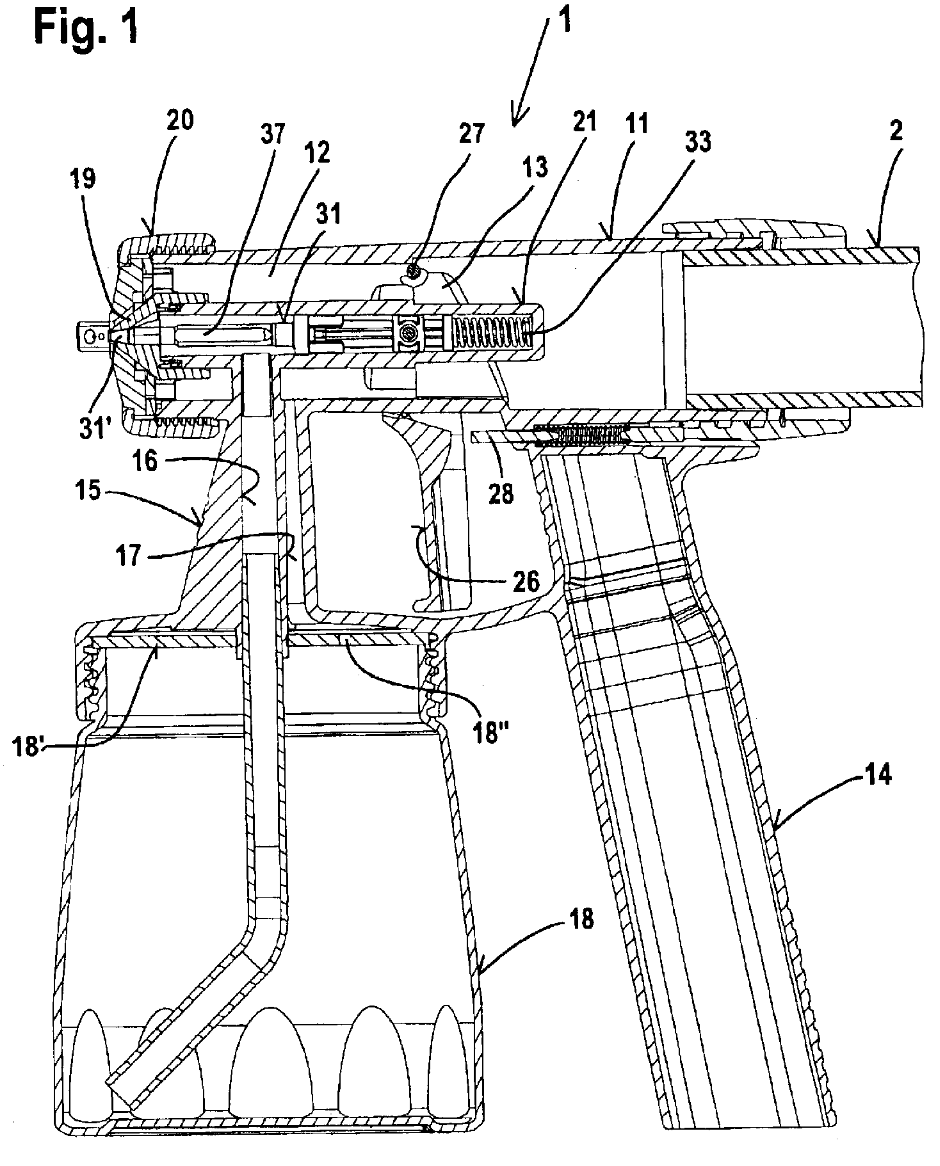

The present invention relates to a spray gun for atomizing fluid media with the help of compressed air, principally consisting of a housing with a handle and an atomizer nozzle which can be connected to a compressed air line, of a guide sleeve supported in the housing equipped with a feed line for the medium to be atomized, with one end of the guide sleeve engaging in the atomizer nozzle, as well as of a valve needle which can be operated against the force of a return spring in order to open the atomizer nozzle by means of a trigger handle which is in a pivoting mounting on the housing.

There are numerous different embodiments of spray guns of prior art which have also proven themselves to be effective in practice. In such embodiments, the valve needle projects out of the guide sleeve on the side facing away from the atomizer nozzle and also out of the housing of the spray gun, while a trigger handle in a pivoting mounting on the housing acts on the spray gun. The valve needle has a special seal in the guide sleeve to prevent the medium to be applied from leaking out of the interior of the guide sleeve. This is achieved in that a deformable seal is clamped in between the valve needle and the guide sleeve by means of a further sleeve which can be screwed into the guide sleeve.

Assembling the valve needle in the guide sleeve is difficult and time-consuming, since the clamping force which acts on the seal must be set exactly. This is because, if the preload on the seal is too great, the valve needle can only be moved by applying considerable force to it, while on the other hand if the preload is insufficient then there is a significant risk that medium will leak out during operation through the two ring gaps which are to be sealed. The stuffing gland arranged in the guide sleeve therefore represents a degree of uncertainty as far as achieving a correct seal is concerned. Furthermore, the seal is a considerable cost factor, since the stuffing gland is assembled from several interacting components which are subject to wear and also have to be replaced from time to time.

The purpose of the present invention is therefore to create a spray gun of the aforementioned type in such a way that straightforward assembly of the valve needle is possible within a short period of time and that a reliable means is provided to prevent the medium leaking out from the interior of the guide sleeve. The construction complexity by which this is to be achieved should be kept at a low level, therefore permitting economical manufacture and assembly of the spray gun. Also, the susceptibility to faults should be reduced over a long service life.

In the present invention, this is achieved in a spray gun in accordance with the pre-characterizing clause of claim 1 in that the valve needle is located in a positive connection with the trigger handle in the area of the guide sleeve by means of a hinge pin which passes through the valve needle and the guide sleeve and that a seal is inserted in the guide sleeve with a U-shaped cross section, the seal being located between the feed line and the hinge pin, with the valve needle being held in a movable arrangement in the seal.

It is advantageous in this arrangement for the valve needle to be provided with a thickened portion in the area of a bore which accommodates the hinge pin, with the thickened portion being adapted to the internal jacket surface of the guide sleeve, and for the valve needle to be provided with a collar in the end area facing away from the atomizer nozzle, serving as a stop for the return spring which is inserted in between the collar and a base of the guide sleeve.

The seal which accommodates the valve needle should be equipped with one or more lugs projecting along the length of the valve needle on one of its two sides, with each of the lugs having a slot and with projections formed on the valve needle engaging in the slots or between two lugs.

For the purpose of positionally-oriented assembly of the valve needle, it is furthermore advantageous for one or more, or in a preferred embodiment two, diametrically opposed contact surfaces to be formed onto the valve needle, in which case the contact surfaces should be worked into the valve needle between the tip of the valve needle and the seal which holds it.

The guide sleeve can be held in a partition wall of the housing in a straightforward way and be used to provide a seal in the atomizer nozzle with the help of a lip seal, as well as being supported axially on the partition wall of the housing by means of a stop surface.

Furthermore, it is advantageous for the valve needle to be made in one piece from plastic.

If a spray gun is configured in accordance with the present invention, then not only will reliable operation be assured at all times, but also the valve needle can be installed in the guide sleeve in a positionally-oriented manner without difficulty and excluding the possibility of the medium to be applied leaking out. This is because an assembly tool can be used to insert the valve needle together with the seal through which it is inserted and the return spring into the guide sleeve which is closed at one end, with the aforementioned components being inserted in such a way that the hinge pin by means of which the valve needle is held in a positive connection with the trigger handle can be installed without difficulty. There is no need to clamp special seals in this embodiment, and also only a few components are required to enable the stored medium to be applied in a metered fashion.

Economical production is possible since nearly all components, in particular also the single-piece valve needle, can be manufactured from plastic. Furthermore, the design ensures that malfunctions and wear to the few components which are to be moved during operation are practically excluded, so therefore the spray gun configured in accordance with the proposed invention can be guaranteed to achieve a lengthy service life.

Figure 2:
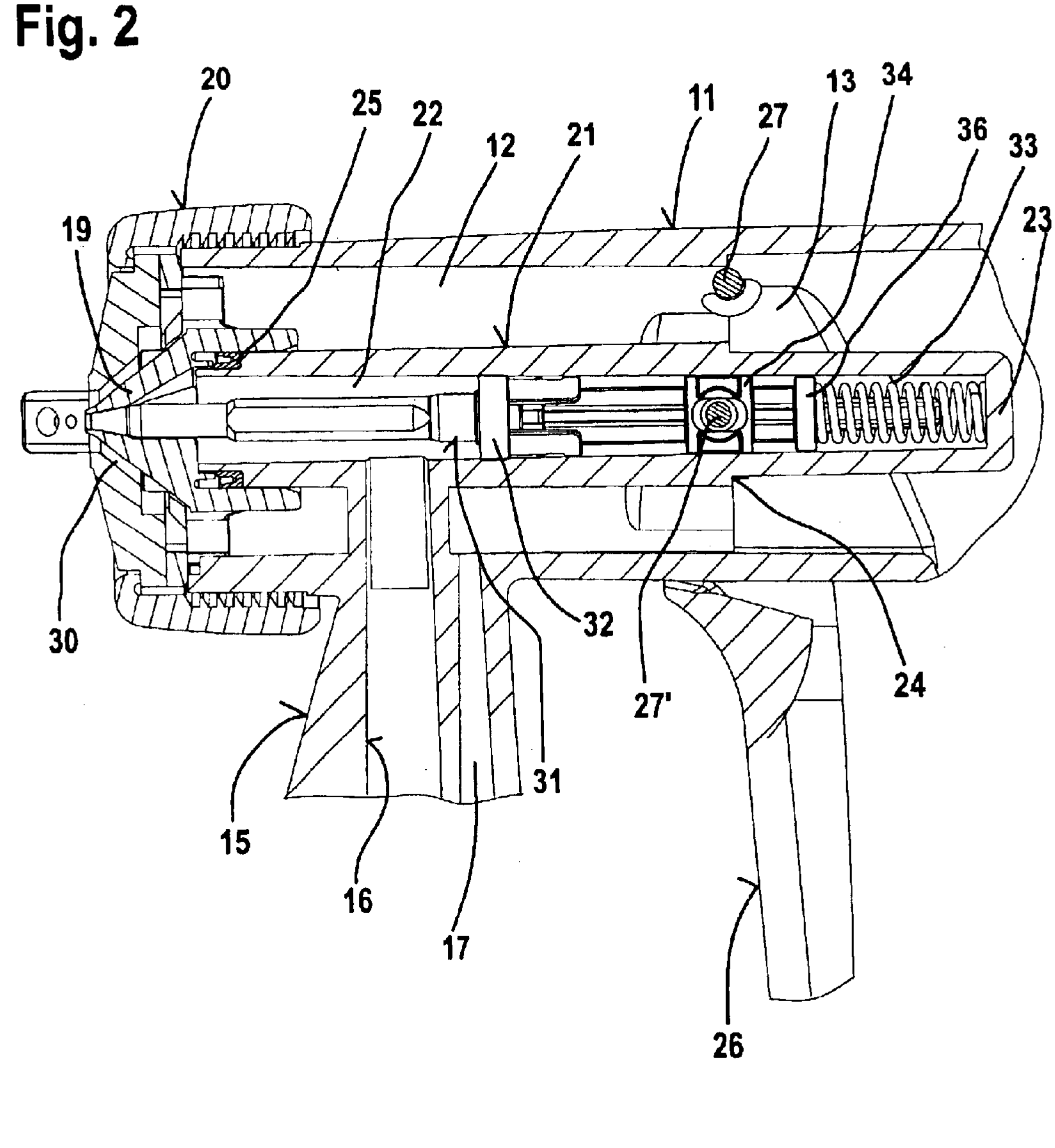
Figure 3:
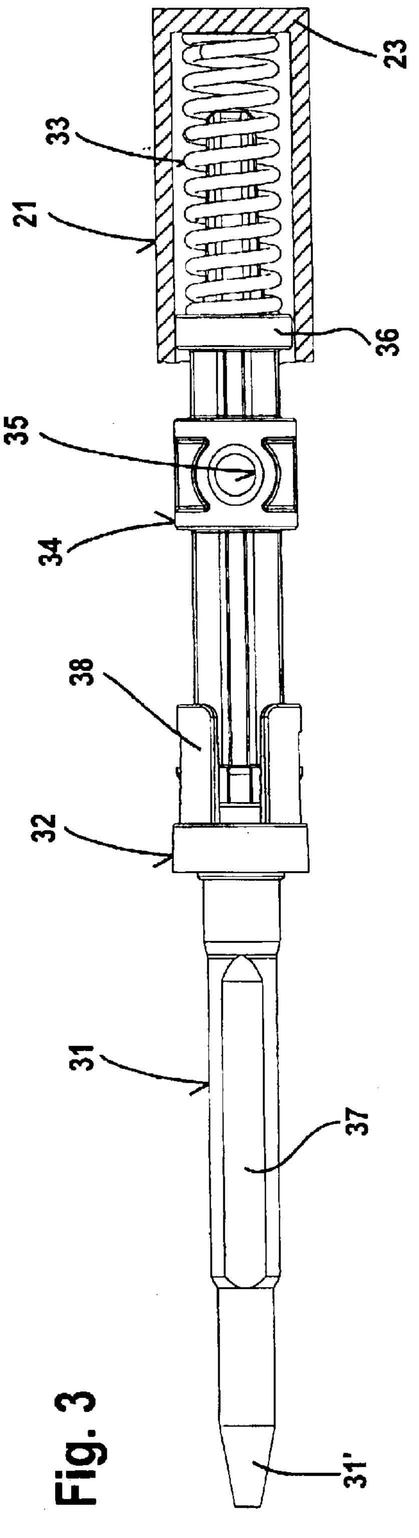
Figure 4:
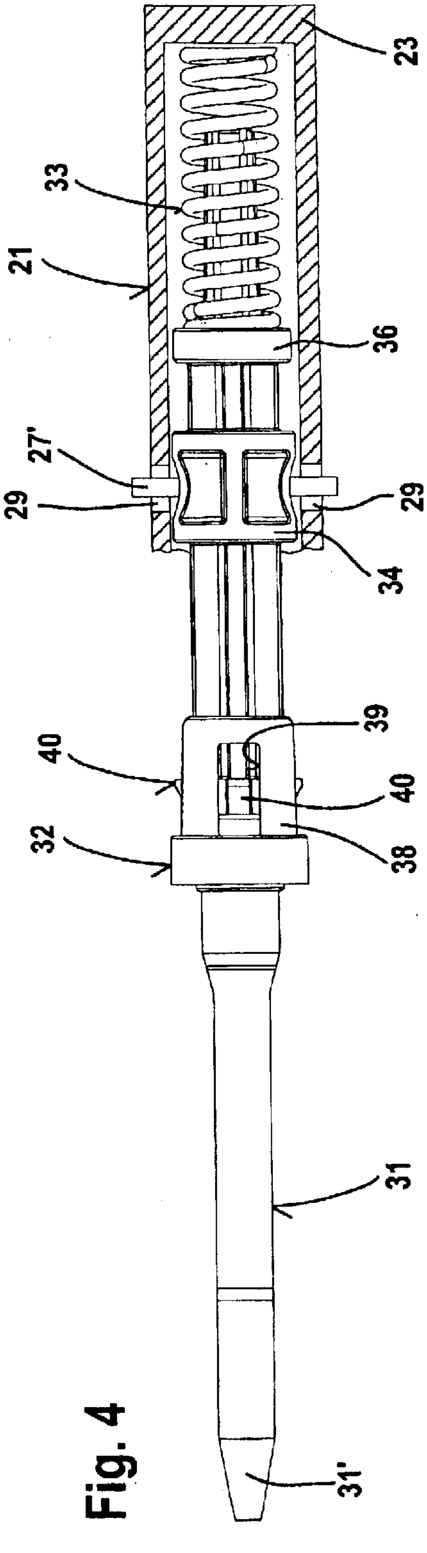

The drawing shows a sample embodiment of a spray gun configured in accordance with the present invention, the details of which are explained below. In the drawing, the figures of which all show axial sections, FIG. 1 shows the spray gun with all its components, FIG. 2 shows a section through the spray gun in accordance with FIG. 1 in a magnified view, and FIGS. 3 and 4 show the valve needle used in the spray gun in accordance with FIG. 1, in different installation positions.

The spray gun shown in FIG. 1 and identified with the number 1 is used for atomizing fluid media by means of compressed air and its principal components include a pistol-shaped housing 11 on which a handle 14 and a joining piece 15 for holding a reservoir tank 18 are formed, an atomizer nozzle 19 screwed onto the housing 11 at one end by means of a union nut 20 and a valve needle 31 which is arranged in a movable location in a guide sleeve 21. The housing 11 has a compressed air line 2 connected to it from which compressed air flows into the interior 12 of the housing 11 and flows out through ducts 30 provided in the atomizer nozzle 19. When the atomizer nozzle 19 is open, the medium to be applied is drawn from the interior 22 of the atomizer nozzle 19 and is atomized.

The guide sleeve 21 has a U-shaped cross section and is held in a partition wall 13 of the housing 11 as well as in the atomizer nozzle 19. To this end, a contact surface 24 is formed onto the guide sleeve 21, by means of which the guide sleeve 21 is supported against the partition wall 13, and a lip seal 25 is placed on the end of the guide sleeve 21 facing away from the atomizer nozzle 19, so that the medium from the interior 22 of the guide sleeve 21 can only emerge via the atomizer nozzle 19.

The medium to be applied flows into the interior 22 of the guide sleeve 21 via a feed line 16 which is formed in the joining piece 15 onto which a reservoir tank 18 is screwed. To achieve this, a line 17 or a bore 18" is worked into the joining piece 16 as well as into a seal 18' lying on the tank 18, with the interior of the tank 18 being connected to the interior 12 of the housing 11 by means of the line 17 or the bore 18". As a result, compressed air acts on the medium in the tank 18, forcing it into the interior 22 of the guide sleeve 21.

A trigger handle 26 is provided to activate the valve needle 31 inserted in the guide sleeve 21, this trigger handle 26 being held in a pivoting mounting in the housing 11 by means of a hinge pin 27 and in a positive connection with the valve needle by means of a further hinge pin 27'. There is a thickened portion 34 formed on the valve needle 31 for this purpose and a bore 35 is provided in the thickened portion 34 in order to accommodate the hinge pin 27'. In addition, an axially aligned slot 29 is worked into the housing 11 on both sides in the area of the hinge pin 27', so that the hinge pin 27' can be moved in accordance with the movement of the trigger handle 26 which has a stop 28 associated with it for setting and limiting the movement.

As can be seen in particular in FIGS. 3 and 4, the valve needle 31 is provided with two diametrically opposed contact surfaces 37, with the effect that the valve needle 31, together with a seal 32 placed thereupon, can be installed in the guide sleeve 21 in a positionally-oriented manner using an assembly fixture. A return spring 33 is installed in the guide sleeve 21 prior to this, the return spring 33 resting on a base 23 of the guide sleeve 21 and against a collar 36 formed onto the valve needle 31. When opening the atomizer nozzle 19, it is necessary to use the trigger handle 26 to overcome the force of the return spring 33; as soon as no more force is applied to the trigger handle 26, the atomizer nozzle 19 into which the tip 31' of the valve needle 31 projects is automatically closed by means of the return spring 33.

Two formed lugs 38 with slots 39 in them are provided to hold the seal 32 in which the valve needle 31 is inserted in an axially movable arrangement. Projections 40 emerging radially from the valve needle 31 engage in the slots 39 or between the two lugs 38. In this way, it is assured that the seal 32 remains in the assigned position even when the valve needle 31 is moved. Furthermore, the seal 32 ensures that no medium can leak from the interior 22 of the guide sleeve 21 and reach the hinge pin 27', or can emerge from the bore 35 in the valve needle 31 as well as from the slots 29 worked into the housing 11.

What is claimed is:

1. A spray gun (1) for atomizing fluid with compressed air, the spray gun comprising a housing (11), a handle (14) fixed to said housing, an atomizer nozzle (19) which is placed in communication with a compressed air line (2), a guide sleeve (21) supported in said housing (11) and provided with a feed line (16) for the fluid to be atomized, with one end of said guide sleeve (21) engaging in said atomizer nozzle (19), and a valve needle (31) which can be operated against the force of a return spring (33) in order to open said atomizer nozzle (19) by means of a trigger (26) pivotally mounted on said housing (11), wherein said valve needle (31) is connected to the trigger (26) in an area of said guide sleeve (21) by means of a hinge pin (27') which passes through said valve needle (31) and said guide sleeve (21), and wherein a seal (32) is disposed in said guide sleeve (21 ), which is provided with a U-shaped cross section, the seal (32) being located between the feed line (16) and the hinge pin (27'), with said valve needle (31) being held in a movable arrangement in the seal (32).

2. The spray gun in accordance with claim 1, wherein said valve needle (31) is provided with a thickened portion (34) in an area of a bore (35) which accommodates the hinge pin (27'), the thickened portion (34) being complementary to an internal surface of said guide sleeve (21).

3. The spray gun in accordance with claim 1, wherein said valve needle (31) is provided with a collar (36) in an end area removed from said atomizer nozzle (19), the collar serving as a stop for the return spring (33) which is disposed between the collar (36) and a base (23) of said guide sleeve (21).

4. The spray gun in accordance with claim 1, wherein the seal (32) accommodates said valve needle (31) and is provided with lugs (38) projecting along the length of said valve needle (31) on both sides, each of the lugs (38) having a slot (39), and projections (40) formed on said valve needle (31) and engaging in at least one of the slots (39) and between two of the lugs (38).

5. The spray gun in accordance with claim 1, wherein said valve needle (31) comprises diametrically opposed contact surfaces (37) formed on said valve needle (31).

6. The spray gun in accordance with claim 5, wherein the contact surfaces (37) on said valve needle (31) are disposed between a tip (31') of said valve needle (31) and the seal (32).

7. The spray gun in accordance with claim 1, wherein said guide sleeve (21) is held in a partition wall (13) of said housing (11).

8. The spray gun in accordance with claim 7, wherein a lip seal (25) is mounted on said guide sleeve (21) to provide a seal in said atomizer nozzle (19), and said guide sleeve is supported axially on the partition wall (13) of said housing (11) by means of a stop surface (24).

9. The spray gun in accordance with claim 1, wherein said valve needle (31) comprises a single unitary piece of plastic.

* * * * *